US006904316B2

(12) United States Patent
Kramer (10) Patent No.: US 6,904,316 B2
(45) Date of Patent: Jun. 7, 2005

(54) CARDIAC RHYTHM MANAGEMENT SYSTEM WITH MAXIMUM TRACKING RATE (MTR) HYSTERESIS

(75) Inventor: Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 629 days.

(21) Appl. No.: 10/012,887

(22) Filed: Nov. 6, 2001

(65) Prior Publication Data

US 2003/0088287 A1 May 8, 2003

(51) Int. Cl.[7] .............................................. A61N 1/362
(52) U.S. Cl. ......................................................... 607/9
(58) Field of Search ............................ 607/4, 9, 14, 15, 607/17, 25

(56) References Cited

U.S. PATENT DOCUMENTS

| | | | | |
|---|---|---|---|---|
| 4,230,120 | A | 10/1980 | McDonald | 128/419 PT |
| 4,233,985 | A | 11/1980 | Hartlaub et al. | 128/419 PG |
| 4,236,522 | A | 12/1980 | McDonald et al. | 128/419 PG |
| 4,241,736 | A | 12/1980 | Rossing et al. | 128/419 PG |
| 4,250,883 | A | 2/1981 | Thompson | 128/419 PG |
| 4,253,466 | A | 3/1981 | Hartlaub et al. | 128/419 PG |
| 4,257,423 | A | 3/1981 | McDonald et al. | 128/419 PG |
| 4,263,915 | A | 4/1981 | McDonald et al. | 128/419 PG |
| 4,267,843 | A | 5/1981 | McDonald et al. | 128/419 PT |
| 4,273,132 | A | 6/1981 | Hartlaub et al. | 128/419 PG |
| 4,273,133 | A | 6/1981 | Hartlaub et al. | 128/419 PG |
| 4,275,738 | A | 6/1981 | McDonald et al. | 128/419 PG |
| 4,276,883 | A | 7/1981 | McDonald et al. | 128/419 PT |
| 4,344,437 | A | 8/1982 | Markowitz | 128/419 PG |
| 4,401,120 | A | 8/1983 | Hartlaub et al. | 128/419 PT |
| 4,515,159 | A | 5/1985 | McDonald et al. | 128/419 PG |
| 4,550,370 | A | 10/1985 | Baker | 364/413 |
| 4,945,909 | A | 8/1990 | Fearnot et al. | 128/419 PG |
| 5,144,949 | A | 9/1992 | Olson | 128/419 PG |

(Continued)

FOREIGN PATENT DOCUMENTS

EP          0726082          8/1996          ........ A61N/1/368

*Primary Examiner*—Kennedy Schaetzle
*Assistant Examiner*—Kristen Mullen
(74) *Attorney, Agent, or Firm*—Schwegman, Lundberg, Woessner & Kluth, P.A.

(57) ABSTRACT

A cardiac rhythm management system provides both a safe maximum pacing rate limit and a physiological maximum pacing rate limit. The present subject matter provides a solution to problems associated with the use of a single maximum tracking rate (MTR). In one embodiment, the present subject matter utilizes two MTRs, where the first is a normal MTR and the second is a hysteresis MTR. In one embodiment, the hysteresis MTR is set higher than the normal MTR. The hysteresis MTR functions as a maximum pacing rate limit while tracking an atrial rate until the atrial rate exceeds the hysteresis MTR limit. When the atrial rate exceeds the hysteresis MTR limit, the maximum pacing rate limit is set to the normal MTR. Once the atrial rate falls below a predetermined threshold, the maximum pacing rate limit is set to the hysteresis MTR. The predetermined threshold may be set to the normal MTR, the hysteresis MTR, or other rates. In one embodiment, changing the maximum pacing rate limit in this fashion allows for uninterrupted pacing treatment for patients, such as congestive heart failure (CHF) patients, who may display fast but physiologically normal heart rates and need cardiac resynchronization therapy (CRT) at such fast heart rates. Such a pacing treatment provides for a more rapid and natural maximum pacing rate limit for the patient, while still protecting the patient from being paced at abnormally high rates.

22 Claims, 5 Drawing Sheets

U.S. PATENT DOCUMENTS

| | | | |
|---|---|---|---|
| 5,247,930 A | 9/1993 | Begemann et al. | 607/11 |
| 5,303,702 A | 4/1994 | Bonnet et al. | 607/20 |
| 5,342,405 A | 8/1994 | Duncan | 607/17 |
| 5,391,189 A | 2/1995 | van Krieken et al. | 607/17 |
| 5,531,771 A * | 7/1996 | van der Veen | 607/9 |
| 5,674,257 A | 10/1997 | Stroebel et al. | 607/17 |
| 5,733,312 A | 3/1998 | Schloss et al. | 607/17 |
| 5,968,081 A | 10/1999 | Levine | 607/9 |
| 5,983,138 A * | 11/1999 | Kramer | 607/9 |
| 5,999,854 A | 12/1999 | Deno | 607/18 |
| 6,119,040 A | 9/2000 | Chirife | 607/18 |
| 6,216,035 B1 | 4/2001 | Stahl et al. | 607/9 |
| 6,311,088 B1 | 10/2001 | Betzold et al. | 607/14 |
| 6,636,766 B2 * | 10/2003 | Bornzin et al. | 607/19 |
| 2002/0087198 A1 * | 7/2002 | Kramer et al. | 607/9 |

* cited by examiner

CARDIAC RHYTHM MANAGEMENT SYSTEM WITH MAXIMUM TRACKING RATE (MTR) HYSTERESIS

FIELD OF THE INVENTION

The present invention relates generally to cardiac rhythm management devices, and more particularly, but not by way of limitation, to a cardiac rhythm management system with maximum pacing rate hysteresis.

BACKGROUND INFORMATION

When functioning properly, the human heart maintains its own intrinsic rhythm, and is capable of pumping adequate blood throughout the body's circulatory system. However, some people have abnormal cardiac electrical conduction patterns and irregular cardiac rhythms that are referred to as cardiac arrhythmias. Such arrhythmias result in diminished blood circulation. One mode of treatment includes use of a cardiac rhythm management system. Such systems are often implanted in a patient and deliver electrical stimulation therapy to the patient's heart.

Cardiac rhythm management systems include, among other things, pacemakers, also referred to as pacers. Pacemakers deliver timed sequences of low energy electrical stimuli, called pacing pulses, to the heart, typically via one or more intravascular leadwires or catheters (referred to as "leads") each having one or more electrodes disposed in or about the heart. Heart contractions are initiated in response to such pacing pulses (this is referred to as "capturing" the heart). Pacemakers also sense electrical activity of the heart in order to detect depolarization signals corresponding to the electrical excitation associated with heart contractions. This function is referred to as cardiac sensing. Cardiac sensing is used to time the delivery of pacing pulses with the heart's intrinsic (native) rhythm. By properly timing the delivery of pacing pulses, the heart can be induced to contract in a proper rhythm, greatly improving its output of blood. Pacemakers are often used to treat patients with bradyarrhythmias (also referred to as bradycardias), that is, hearts that beat too slowly. For that application, the pacemakers may operate in an "on-demand" mode, such that a pacing pulse is delivered to the heart only in absence of a normally timed intrinsic contraction. The on-demand pacing function is often embodied in algorithms exhibiting pace inhibition, in which pacing in a lead is prevented (inhibited) for one heart beat when a cardiac depolarization is detected in the same lead prior to the pace. In bradycardia patients, for example, on-demand pacing can ensure that pacing pulses are delivered only when the patient's intrinsic heart rate drops below a predetermined minimum pacing rate limit, referred to as a lower rate limit (LRL). Some pacemakers provide for two lower rate limits, a first LRL, sometimes called a normal LRL, to provide a minimum necessary heart rate during awake or exercise periods, and a second LRL, sometimes called a hysteresis LRL, to allow the heart to reach naturally slower rates during sleep. When the patent's heart rate falls below the hysteresis LRL, the pacemaker switches to the normal LRL to ensure the patient will have sufficient cardiac output by protecting the patient against abnormally slow heart rates.

Cardiac rhythm management systems also include cardioverters/defibrillators that are capable of delivering higher energy electrical stimuli to the heart. Defibrillators are often used to treat patients with tachyarrhythmias (also referred to as tachycardias), that is, hearts that beat too quickly. Such too-fast heart rhythms also cause diminished blood circulation because the heart is not allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia and allows the heart to reestablish a normal rhythm for efficient pumping of blood.

Cardiac rhythm management systems also include, among other things, pacemaker/defibrillators that combine the functions of pacemakers and defibrillators, drug delivery devices, and any other implantable or external systems or devices for diagnosing or treating cardiac arrhythmias.

One problem faced by cardiac rhythm management systems is the treatment of congestive heart failure (also referred to as "CHF"). CHF, which can result from long-term hypertension, is a condition in which the muscle in the walls of at least one of the right and left sides of the heart deteriorates. By way of example, suppose the muscle in the walls of the left side of the heart deteriorates. As a result, the left atrium and left ventricle become enlarged, and the heart muscle displays less contractility, often associated with unsynchronized contraction patterns. This decreases cardiac output of blood, and in turn, may result in an increased heart rate and less resting time between heart contractions. This condition may be treated by conventional dual-chamber pacemakers and a new class of biventricular (or multisite) pacemakers that are termed cardiac resynchronization therapy (CRT) devices. A conventional dual-chamber pacemaker typically paces and senses one atrial chamber and one ventricular chamber. A pacing pulse is timed to be delivered to the ventricular chamber at the end of a programmed atrio-ventricular delay, referred to as AV delay, which is initiated by a pace delivered to or an intrinsic depolarization detected from the atrial chamber. This mode of pacing is sometimes referred to as an atrial tracking mode. The heart can be paced with a shortened AV delay to increase the resting time between heart contractions to increase the amount of blood that fills the ventricular chamber, thus increasing the cardiac output. Biventricular or other multi-site CRT devices can pace and sense three or four chambers, usually including the right atrial chamber and both right and left ventricular chambers. By pacing both right and left ventricular chambers, the CRT device can restore a more synchronized contraction of the weakened heart muscle, thus increasing the heart's efficiency as a pump. When treating CHF either with conventional dual-chamber pacemakers or CRT devices, it is critical to pace the ventricular chambers continuously to shorten the AV delay or to provide resynchronizing pacing, otherwise the patient will not receive the intended therapeutic benefit. Thus the intention for treating CHF patients with continuous pacing therapy is different from the intention for treating bradycardia patients with on-demand pacing therapy, which is active only when the heart's intrinsic (native) rhythm is abnormally slow.

Conventional pacemakers and CRT devices in current use rely on conventional on-demand pacing modes to deliver ventricular pacing therapy. These devices need to be adapted to provide a continuous pacing therapy required for treatment of CHF patients. One particular problem in these devices is that they prevent pacing when the heart rate rises above a maximum pacing limit. One such maximum pacing limit is a maximum tracking rate (MTR) limit. "MTR" and "MTR interval," where an "MTR interval" refers to a time interval between two pacing pulses delivered at the MTR, are used interchangeably, depending on convenience of description, throughout this document. The MTR presents a problem particularly for CHF patients, who typically have elevated heart rates to maintain adequate cardiac output. When a pacemaker or CRT device operates in an atrial tracking mode, it senses the heart's intrinsic rhythm that originates in the right atrial chamber, that is, the intrinsic atrial rate. As long as the intrinsic atrial rate is below the MTR, the device will pace one or both ventricular chambers after an AV delay. If the intrinsic atrial rate rises above the MTR, the device will limit the time interval between adjacent ventricular pacing pulses to an interval corresponding to the MTR, that is, ventricular pacing rate will be limited to the MTR. In this case, the heart's intrinsic contraction rate is faster than the maximum pacing rate allowed by the pacing device so that after a few beats, the heart will begin to excite the ventricles intrinsically at the faster rate, which causes the device to inhibit the ventricular pacing therapy due to the on-demand nature of its pacing algorithm. The MTR is programmable in most conventional devices so that the MTR can be set above the maximum intrinsic atrial rate associated with the patient's maximum exercise level, that is, above the physiological maximum atrial rate. However, many patients suffer from periods of pathologically fast atrial rhythms, called atrial tachyarrhythmia. Also some patients experience pacemaker-mediated tachycardia (PMT), which occurs when ventricular pacing triggers an abnormal retrograde impulse back into the atrial chamber that is sensed by the pacing device and triggers another ventricular pacing pulse, creating a continuous cycle of pacing-induced tachycardia. During these pathological and device-mediated abnormally elevated atrial rhythms, the MTR provides a protection against pacing the patient too fast, which can cause patient discomfort and adverse symptoms. Thus, to protect the patient against abnormally fast pacing, the MTR often is programmed to a low, safe rate that is actually below the physiological maximum heart rate. For many CHF patients with elevated heart rates, this means that they cannot receive the intended pacing therapy during high but physiologically normal heart rates, thus severely limiting the benefit of pacing therapy and the level of exercise they can attain. Therefore, there is a need for addressing this MTR-related problem in therapeutic devices for CHF patients as well as other patients for whom pacing should not be suspended during periods of fast but physiologically normal heart rates.

SUMMARY OF THE INVENTION

The present disclosure describes, among other things, a cardiac rhythm management system and method providing both a safe maximum pacing rate limit and a physiological maximum pacing rate limit. The present subject matter provides a solution to problems associated with the use of a single maximum tracking rate (MTR). In one embodiment, the present subject matter utilizes two MTRs, where the first is a normal MTR and the second is a hysteresis MTR. A heart rate is measured. In one embodiment, the heart rate is measured from a ventricular location. In an alternative embodiment, the heart rate is measured from an atrial location. In one embodiment, the hysteresis MTR is set higher than the normal MTR. The hysteresis MTR functions as a maximum pacing rate limit until the heart rate exceeds the hysteresis MTR limit. When the heart rate exceeds the hysteresis MTR limit, the maximum pacing rate limit is set to the normal MTR. Once the heart rate falls below the normal MTR, the maximum pacing rate limit is set to the hysteresis MTR, or alternatively, once the heart rate falls below the hysteresis MTR, the maximum pacing rate limit is set to the hysteresis MTR.

By utilizing a hysteresis MTR, two or more MTRs are provided for handling fast heart rates having either physiological or pathological origins. The normal MTR prohibits pacing at a rate that may cause adverse effect on a patient. The hysteresis MTR, on the other hand, allows for uninterrupted pacing treatment for patients, such as congestive heart failure (CHF) patients, who may display fast but physiologically normal heart rates but still benefit from cardiac resynchronization therapy (CRT) at such fast heart rates. In other words, the present subject matter provides the patient with a treatment using a variable maximum pacing rate limit that is physiologically safe and beneficial to the patient.

In one embodiment, the hysteresis MTR interval is set equal to the sum of the programmed post-ventricular atrial refractory period (PVARP) plus the atrioventricular pacing delay (AV delay). In another embodiment, the hysteresis MTR interval is set equal to the sum of the programmed PVARP plus the AV delay intervals plus a sensing window interval that allows sufficient time for sensing and detecting an atrial depolarization following after the PVARP expires.

In one embodiment, the PVARP is set to a first set value when the maximum ventricular pacing rate is set to the normal MTR, and is set to a second set value when the maximum ventricular pacing rate is set to the hysteresis MTR. In an alternative embodiment, the PVARP is set dynamically as a function of a heart rate that is between a lower rate limit (LRL) and the hysteresis MTR.

This summary is intended to provide an overview of the subject matter of the present patent application. It is not intended to provide an exhaustive or exclusive explanation of the invention. The detailed description is included to provide further information about the subject matter of the present patent application.

DETAILED DESCRIPTION

In the following detailed description of the preferred embodiments, reference is made to the accompanying drawings that form a part hereof, and in which are shown by way of illustration specific embodiments in which the invention may be practiced. It is understood that other embodiments may be utilized, and structural changes may be made without departing from the scope of the present subject matter.

The present subject matter is described in applications involving implantable cardiac rhythm management systems including, but not limited to, pacemakers, cardioverter/defibrillators, pacemaker/defibrillators, and biventricular or other multi-site cardiac resynchronization therapy (CRT) devices. However, it is understood that the present methods and apparatus may be employed in unimplanted devices, including, but not limited to, external pacemakers, cardioverter/defibrillators, pacemaker/defibrillators, biventricular or other multi-site CRT devices, monitors, programmers and recorders.

Figure 1:
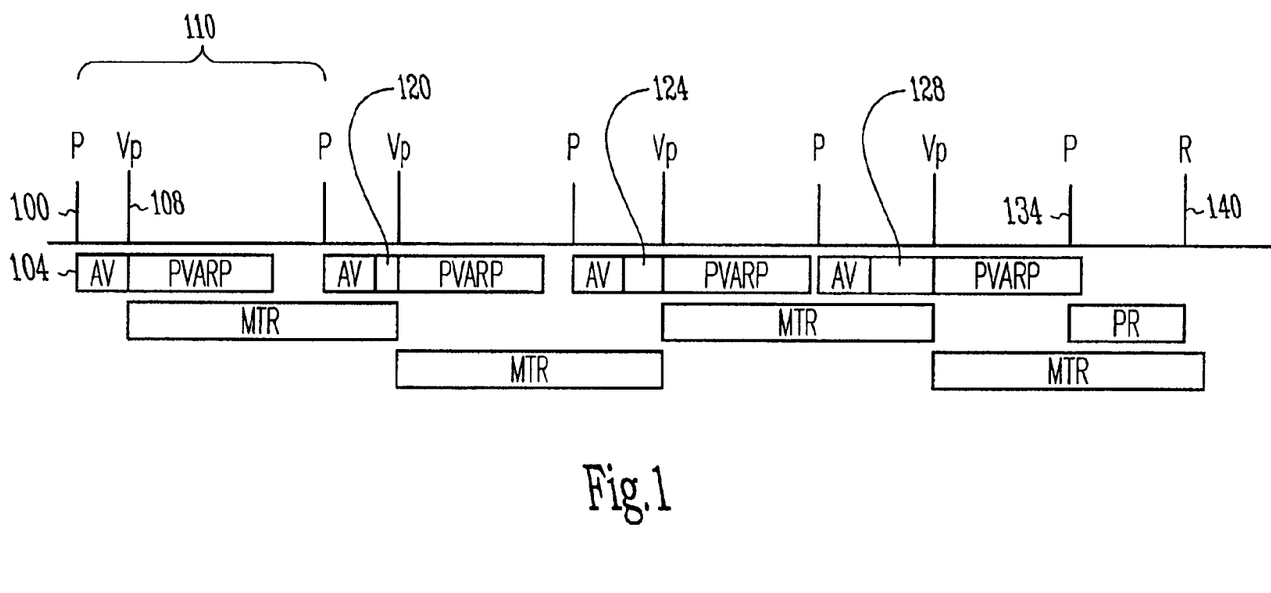
FIG. 1 is a timing schematic illustrating one embodiment of a pacing scheme utilizing a single MTR.

Referring now to FIG. 1, there is shown one embodiment in which an interval between a sensed atrial depolarization and a subsequent ventricular depolarization are extended through the use of a single MTR. At 100, an atrial depolarization is sensed. After a programmed AV delay 104, a ventricular pacing pulse is delivered at 108. In one embodiment, the ventricular pacing pulses have a maximum limit of the single MTR. The atrial rate then increases at 110 (time interval between atrial depolarizations decreases, leading to a rise in the atrial rate). At this point, the atrial rate has exceeded the MTR, but the MTR remains as the limit for ventricular pacing. Thus, the time interval between atrial and ventricular depolarization, i.e., an actual AV delay, increases, as indicated at 120. On each subsequent cycle when the atrial rate exceeds the MTR, the actual AV delay increases, as shown at 124 and 128. At 128, the actual AV delay becomes so great that an atrial depolarization 134 is not sensed, as atrial depolarization 134 occurs during the post-ventricular atrial refractory period (PVARP). Atrial depolarization 134 results in an intrinsic ventricular depolarization 140 (i.e., non-paced ventricular depolarization) which occurs prior to the MTR expiring. As a result, CRT is lost and/or compromised when the atrial rate rises above the MTR.

The present subject matter provides a solution to this problem, among other problems associated with the use of a single MTR. By utilizing a second MTR, also referred to in this document as the hysteresis MTR, in addition to a first MTR, also referred to in this document as the normal MTR, two or more MTRs are provided to deal with fast atrial rates (e.g., atrial tachycardia rates) having either physiological or pathological origins. In one embodiment, the hysteresis MTR is set higher than the normal MTR. The hysteresis MTR is the maximum pacing rate limit until the heart rate exceeds the hysteresis MTR. The maximum pacing rate limit then falls back to MTR when the heart rate exceeds the hysteresis MTR. Finally, the maximum pacing rate limit reverts to the hysteresis MTR when the heart rate falls below a predetermined threshold. In one embodiment, the predetermined threshold is set to the normal MTR. In an alternative embodiment, the predetermined threshold is set to the hysteresis MTR. Changing the maximum pacing rate limit in this fashion allows for an alternative treatment for patients, such as CHF patients, who display fast heart rates and need CRT at the faster heart rates. This alternative treatment provides for a more rapid and natural maximum pacing rate limit for the patient, but still protects the patient from tracking abnormally high rates by limiting pacing to a lower maximum tracking rate when the heart rate exceeds the hysteresis MTR.

Figure 2:
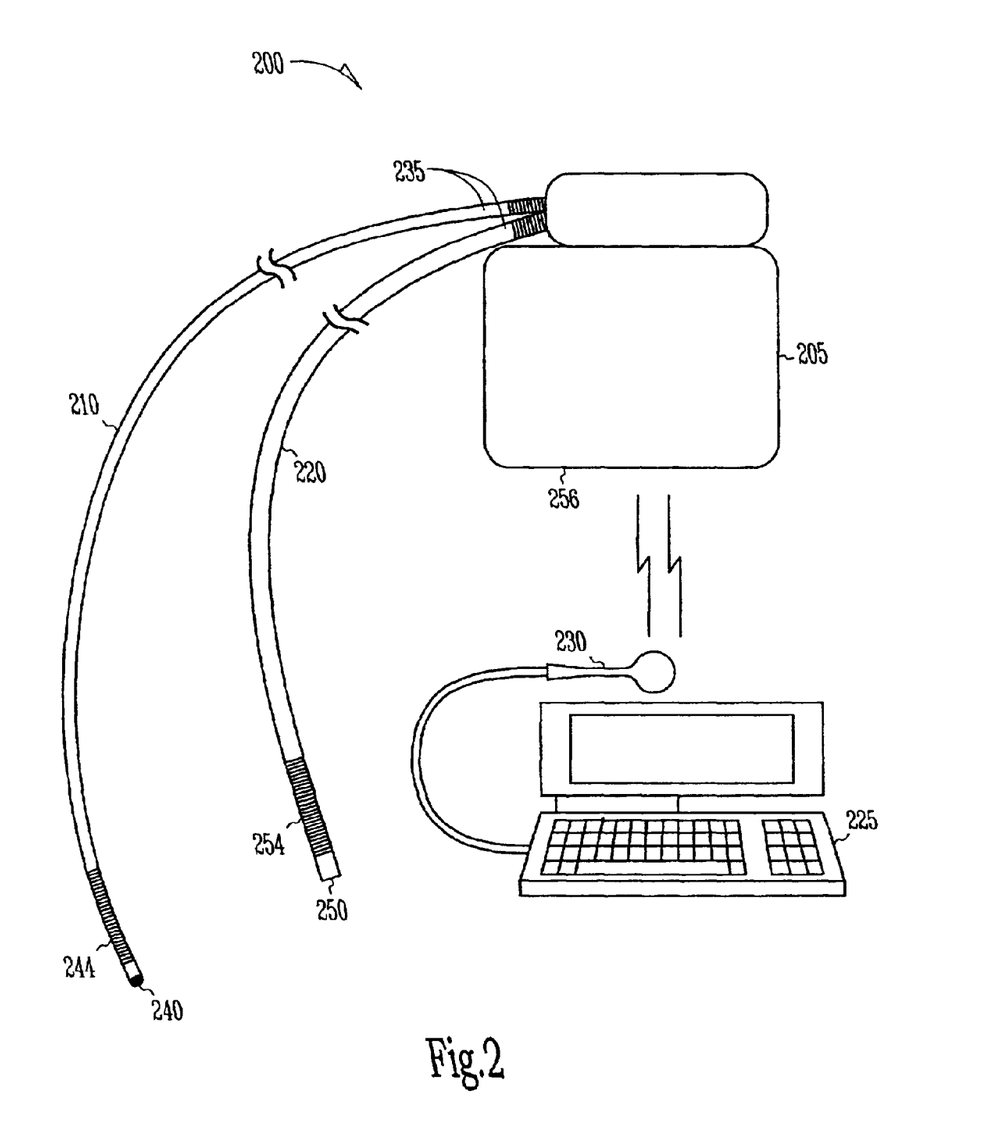
FIG. 2 is a schematic illustrating one embodiment of a cardiac rhythm management device.

Referring now to FIG. 2, there is shown one embodiment of a cardiac rhythm management system 200. The cardiac rhythm management system 200 includes an implantable cardiac rhythm management device 205, also referred to as an implantable pulse generator, which is coupled to a first intravascular endocardial lead 210 and a second intravascular endocardial lead 220. Additional leads may be connected to provide multi-site CRT. System 200 also includes an external programmer 225 wirelessly communicating with device 205 using a telemetry device 230.

Each of leads 210 and 220 includes a proximal end 235 having a connector portion which is coupled to device 205, and a distal end that can be implanted into a heart to sense one or more cardiac signals. Each of leads 210 and 220 includes one or more electrodes at the distal end for sensing cardiac signals and delivering electrical energy pulses (e.g., pacing pulses).

In the embodiment shown in FIG. 2, lead 210 includes one or more electrodes, such as a tip electrode 240 and a ring electrode 244, for sensing cardiac signals and/or delivering pacing therapy. Lead 210 can also include additional electrodes, such as defibrillation electrodes for delivering atrial and/or ventricular cardioversion/defibrillation and/or pacing therapy. Lead 220 includes one or more electrodes, such as a tip electrode 250 and a ring electrode 254, for sensing cardiac signals and/or delivering pacing therapy. Lead 220 optionally also includes additional electrodes, such as defibrillation electrodes for delivering atrial and/or ventricular cardioversion/defibrillation and/or pacing therapy.

Device 205 includes components enclosed in a hermetically-sealed housing 256. Housing 256 can be used as an additional pacing/cardioversion/defibrillation electrode. More generally, the present subject matter works with a variety of other electrode configurations and with a variety of electrical contacts or "electrodes", as are known in the art.

Figure 3:
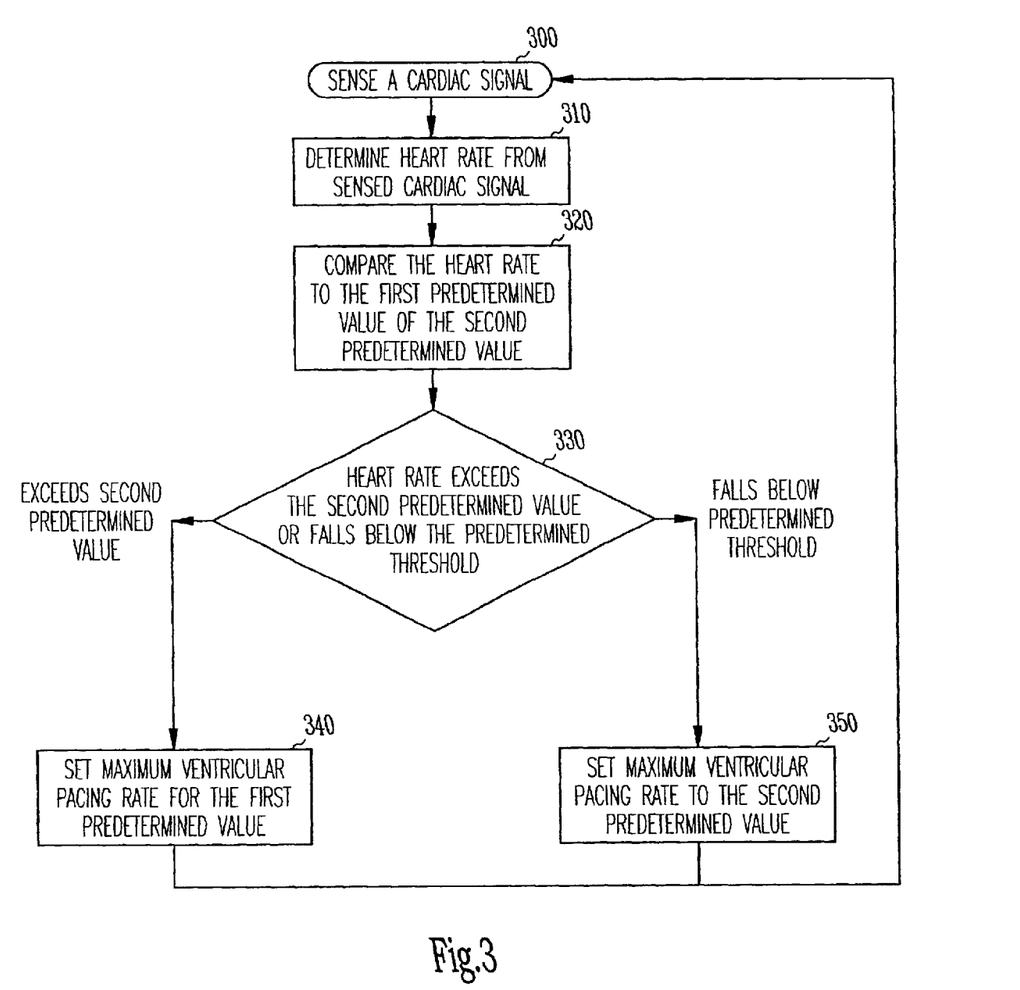
FIG. 3 is a flow chart illustrating one embodiment of the present subject matter.

Referring now to FIG. 3, there is shown one embodiment of a method according to the present subject matter. Once started at 300, a cardiac signal is sensed. At 310, a heart rate is determined from cardiac depolarizations detected in the cardiac signal. In one embodiment, the cardiac signal is sensed from a ventricular location, and the heart rate is determined based on a time interval between two adjacent ventricular depolarizations (R-waves), referred to as an R—R interval or ventricular cycle length. In another embodiment, the heart rate is determined based on an R—R interval value averaged over a predetermined number of ventricular cycles. In an alternative embodiment, the cardiac signal is sensed from an atrial location, the heart rate is determined based on a time interval between two adjacent atrial depolarizations (P-waves), referred to as a P—P interval or an atrial cycle length. In another alternative embodiment, the heart rate is determined based on a P—P interval value averaged over a predetermined number of atrial cycles. At 320, the heart rate is compared to a first predetermined value and a second predetermined value, where the second predetermined value is greater than the first predetermined value. According to one embodiment of the present subject matter, the first predetermined value is a normal MTR and the second predetermined value is a hysteresis MTR, as previously discussed.

At 330, the system determines whether the heart rate exceeds the second predetermined value and whether the heart rate falls below a predetermined threshold. When the heart rate exceeds the second predetermined value, a maximum ventricular pacing rate is set to the first predetermined value, at 340. If, however, at 330 the system detects that the heart rate falls below the predetermined threshold, the system sets the maximum ventricular pacing rate to the second predetermined value at 350. In one embodiment, the predetermined threshold is set to the first predetermined value. In an alternative embodiment, the predetermined threshold is set to the second predetermined value. In an additional embodiment, at 340, when the heart rate exceeds the second predetermined value, the maximum ventricular pacing rate is set to the first predetermined value, and the change of the maximum ventricular pacing rate from the second predetermined value to the first predetermined value is done gradually over a predetermined time interval (i.e., the switch from the hysteresis MTR to the normal MTR is rate-smoothed). The system then returns to 300 to repeat the analysis just described.

In one embodiment, the present subject matter is used in a tracking mode of pacing, in which a maximum pacing rate limit is required. During the tracking mode, an intrinsic depolarization sensed at a first heart site triggers a pace at a second heart site with or without a pre-determined delay. In one embodiment, the tracking mode is an atrial tracking mode, in which the first heart site is in an atrial chamber, typically on the right side of the heart. One example of the atrial tracking mode is a DDD mode, in which a cardiac rhythm management system senses an intrinsic depolarization in the atrial chamber and triggers a pace in the ventricular chamber after a predetermined AV delay. The DDD mode is also an example of a tracking mode combined with on-demand pacing. For example, in the DDD mode, an intrinsic depolarization sensed in the atrial chamber may be followed by an intrinsic depolarization sensed in the ventricular chamber after an intrinsic AV interval (a time interval between an intrinsic atrial depolarization and an adjacently subsequent intrinsic ventricular depolarization) that is shorter than the AV delay. When this occurs, the intrinsic depolarization sensed in the ventricle inhibits the ventricular pace that would occur at the end of the AV delay. In tracking modes, the pacing rate increases in response to the intrinsic heart rate. As long as the heart's intrinsic rhythm is physiologically normal, these modes of operation are safe, but when the intrinsic rhythm becomes abnormally fast, such as during an atrial tachyarrhythmia, tracking might increase the pacing rate to non-physiological and harmful levels. To prevent such occurrences, a tracking mode of operation traditionally provides for a maximum pacing rate limit, the MTR, which limits the time interval between pacing pulses to be no faster than the MTR interval. Tracking modes provide additional protection against pacemaker-mediated tachycardia (PMT), which occurs when a pacing pulse delivered to the second heart site causes a detectable depolarization at the first heart site that triggers another pacing pulse to be delivered to the second heart site again, which continues in a loop. PMT in tracking modes can be prevented by using a post-ventricular atrial refractory period (PVARP), which is a period of time following the pace at the second heart site during which sensing is blocked or ignored (i.e., made refractory) at the first heart site. Also, tracking modes provide for stopping a PMT once it occurs by increasing the duration of the PVARP, called PVARP extension, when a PMT is detected.

CHF patients may benefit from continuous atrial-synchronous ventricular pacing that operates in an atrial tracking mode. The benefit arises from the coordination of the atria and ventricles, and not simply as rate support for the ventricles. Typically, when the atrial rate exceeds the MTR, ventricular pacing is inhibited or non-optimal. Examples of inhibited ventricular pacing include where an intrinsic AV interval resulting from the fast atrial rate causes a ventricular depolarization before the end of the MTR interval, which in turn would cause the ventricular pacing to be inhibited. Additionally, it is possible that by limiting the pacing rate to the MTR, the duration between the atrial and ventricular contractions will be extended, which may lead to non-optimal atrio-ventricular synchrony. To solve this problem, in one embodiment, the present subject matter provides a tracking mode with two MTRs, where the first is a normal MTR and the second is a hysteresis MTR. The values for the normal MTR and the hysteresis MTR are programmable in the cardiac rhythm management system. In one embodiment, the hysteresis MTR is set higher than the normal MTR. The hysteresis MTR functions as the maximum pacing rate limit while tracking a heart rate until the heart rate exceeds the hysteresis MTR limit. When the heart exceeds the hysteresis MTR limit, the maximum pacing rate limit is set to the normal MTR. Once the heart rate falls below a predetermined threshold, the maximum pacing rate limit is set to the hysteresis MTR. In one embodiment, the predetermined threshold is set to the normal MTR. In an alternative embodiment, the predetermined threshold is set to the hysteresis MTR. Thus, the present subject matter provides a tracking mode with, among other things, a safe maximum pacing rate limit and a physiological maximum pacing rate limit.

In another embodiment, the present subject matter is used in a triggered mode of pacing, in which a maximum pacing rate limit is also required. In a triggered mode, an intrinsic depolarization sensed at a heart site triggers one or more pacing pulses to be delivered to that site, and/or to one or more different heart sites, with or without a pre-determined delay. One example of a triggered mode is a VVT mode, in which the cardiac rhythm management system senses an intrinsic depolarization in a ventricular chamber and triggers an immediate pace in the same ventricular chamber. Another example of a triggered mode is an AAT mode, in which the cardiac rhythm management system senses an intrinsic depolarization in an atrial chamber and triggers an immediate pace in the same atrial chamber. Still another example of a triggered mode is a biventricular trigger mode, in which the cardiac rhythm management system senses an intrinsic depolarization in a ventricular site and triggers one or more pacing pulses to be delivered, with or without a predetermined delay, to the same ventricular site, or to one or more different ventricular sites, or to the same ventricular site and one or more different ventricular sites. During triggered modes, a heart chamber is paced at the intrinsic depolarization rate of the chamber. If that intrinsic rate exceeds a maximum pacing rate limit, the triggered pacing of that chamber is inhibited as long as the intrinsic rate remains above the maximum pacing rate limit. For triggered modes, the present subject matter provides a second, hysteresis maximum pacing rate limit with exactly the same behavior as the hysteresis MTR described previously for tracking modes. In one embodiment, the present subject matter provides a triggered mode with two maximum pacing rates, where the first is a normal maximum pacing rate and the second is a hysteresis maximum pacing rate. The values for the normal maximum pacing rate and the hysteresis maximum pacing rate are programmable in the cardiac rhythm management system. In one embodiment, the hysteresis MTR is set higher than the normal MTR. The hysteresis maximum pacing rate functions as the effective maximum pacing rate limit while pacing being triggered by intrinsic depolarizations until the intrinsic heart rate exceeds the hysteresis maximum pacing rate. When the intrinsic heart rate exceeds the hysteresis maximum pacing rate, the effective maximum pacing rate limit is set to the normal maximum pacing rate. Once the intrinsic heart rate falls below a predetermined threshold, the maximum pacing rate limit is set to the hysteresis maximum pacing rate. In one embodiment, the predetermined threshold is set to the normal maximum pacing rate. In an alternative embodiment, the predetermined threshold is set to the hysteresis maximum pacing rate.

In still another embodiment, the present subject matter is used in a rate smoothing mode of pacing, in which a maximum pacing rate limit is also required. The rate smoothing mode operates by adjusting a pacing rate based on a previous heart rate. In one embodiment, the cardiac rhythm management system operating in the rate smoothing mode limits the variation of the pacing rate to a predetermined percentage of the previous heart rate (intrinsic or paced). In one embodiment, a rate smoothing mode is combined with a tracking mode to provide on-demand pacing. Both the tracking mode and rate smoothing mode would increase the pacing rate in response to a heart's intrinsic rhythm. As long as the heart's intrinsic rhythm is physiologically normal, these modes of operation are safe, but when the intrinsic rhythm becomes abnormally fast, such as during an atrial tachyarrhythmia, tracking and rate smoothing modes might increase the pacing rate to non-physiological and harmful levels. To prevent the pacing rate from becoming too fast when the intrinsic heart rate is increasing, a maximum pacing rate is provided so that when the previous heart rate would require pacing at a rate above the maximum pacing rate, the pacing is inhibited as long as the indicated pacing rate remains above the maximum pacing rate. For rate smoothing modes, the present subject matter provides a second, hysteresis maximum pacing rate limit with exactly the same behavior as the hysteresis maximum pacing rate described previously for triggering modes.

In one embodiment, the first predetermined value has a value in the range from 50 to 180 beats/minute, where 120 beats/minute is a possible value. The second predetermined value has a value in the range from 50 to 180 beats/minute, where 140 beats/minute is a possible value. In an alternative embodiment, the second predetermined value (e.g., the hysteresis MTR) differs from the first predetermined value (e.g., the normal MTR) by a predetermined offset. In one embodiment, the predetermined offset is a programmable value in the range of 10 to 100 beats/minute, where 20 beats/minute is a possible value. In another embodiment, the second predetermined value (e.g., the hysteresis MTR) corresponds to the sum of a programmed PVARP plus an AV delay (e.g., the hysteresis MTR interval equals to the sum of the PVARP plus the AV delay). In still another embodiment, the second predetermined value (e.g., the hysteresis MTR) corresponds to the sum of the programmed PVARP plus the AV delay intervals plus a sensing window interval (e.g., the hysteresis MTR interval equals to the sum of the PVARP plus the AV delay plus the sensing window). In one embodiment, the sensing window interval is a programmable value in the range of 0 to 1000 milliseconds, where 200 milliseconds is a possible value. In another embodiment, the sensing window interval is a percentage of the sum of the PVARP plus the AV delay, where the percentage is a programmable value in the range of 0 to 90%, where 50% is a possible value. In a further embodiment, the predetermined time interval over which the maximum ventricular pacing rate is changed from the second predetermined value to the first predetermined value has a value in the range from 0 to 120 seconds, where 10 seconds is a possible value.

In one embodiment, the PVARP is a programmable value, which can be set based on the first predetermined value and the second predetermined value (i.e., the first predetermined value and second predetermined value can be associated with different PVARP settings to provide an adequate atrial sensing time for each rate range). In one embodiment, the PVARP is set to a first set value when the maximum ventricular pacing rate is set to the first predetermined value, and is set to a second set value when the maximum ventricular pacing rate is set to the second predetermined value. In an alternative embodiment, the PVARP is set dynamically as a function of the heart rate between a lower rate limit (LRL) and the hysteresis MTR (second predetermined value). In one such embodiment, the PVARP is set to a first set value at the LRL, and is set to a second set value at the hysteresis MTR, and is set to a value between the first and second set values, in correspondence with distances of the determined heart rate from the LRL and the hysteresis MTR. In another alternative embodiment, the PVARP associated with each MTR can be set such that the sum of the PVARP plus the AV delay is equal to a predetermined MTR interval minus the sensing window interval. In one embodiment, the sensing window interval is a programmable value in the range of 0 to 1000 milliseconds, where 200 milliseconds is a possible value. In an alternative embodiment, the sensing window interval is a percentage of the predetermined MTR interval, where the percentage is a programmable value in the range of 0 to 90%, where 50% is a possible value.

In an additional embodiment, the PVARP having the first set value is extended for at least one cardiac cycle length (a time interval between two consecutive heart contractions sensed from the same lead) after setting the maximum ventricular pacing rate to the first predetermined value when the heart rate exceeds the second predetermined value. In one embodiment, this is done to protect against sensing retrograde atrial events that can lead to a pacemaker-mediated tachycardia (PMT).

In another additional embodiment, PMT can be interrupted by ignoring the atrial sense and not triggering the AV delay for one cardiac cycle every N cycles when the heart rate is above the first predetermined value. In one embodiment, the atrial sense is ignored by extending the PVARP. In another embodiment, the value of N is programmable in the range of 10 to 100, where 25 is a value that can be used.

In still another additional embodiment, atrial depolarizations sensed during the PVARP can cause the maximum ventricular pacing rate to be set to a different value. For example, when an atrial depolarization is detected during the PVARP, the maximum ventricular pacing rate is set to the first predetermined value. This additional embodiment may be added to the present subject matter to allow for the maximum ventricular pacing rate to be changed from the second predetermined value to the first predetermined value. In an additional embodiment, the switch from the second predetermined value to the first predetermined value is also triggered by a ventricular pacing rate that is equal to the second predetermined value, so that when ventricular pacing pulses are delivered at a rate equal to the second predetermined value, the maximum ventricular pacing rate is set to the first predetermined value.

Figure 4:
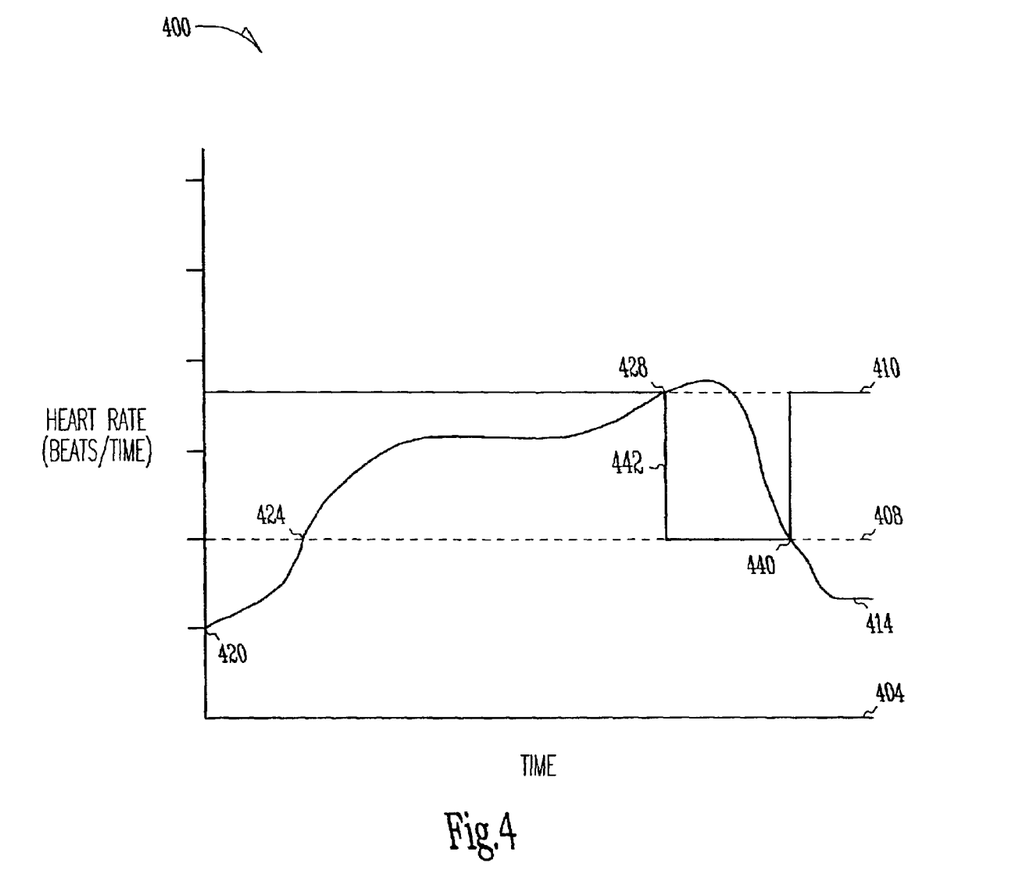
FIG. 4 is a graph of a heart rate and a maximum pacing rate plotted as functions of time according to one embodiment of the present subject matter.

Referring now to FIG. 4, there is shown one embodiment of a heart rate 400 plotted as a function of time 404. In addition, there is shown two lines representing the first predetermined value 408 and the second predetermined value 410. In one embodiment, the first predetermined value 408 represents the normal MTR, and the second predetermined value 410 represents the hysteresis MTR. A curve 414 represents a heart rate as a function of time. The heart rate may be measured from a ventricular chamber or, alternatively, an atrial chamber. A line 442 represents the maximum pacing rate as a function of time. Heart rate 414 starts with an initial value 420. In one embodiment, the maximum pacing rate is initially set to the second predetermined value 410.

As heart rate 414 is determined, the value of heart rate 414 is compared to the first predetermined value 408 and the second predetermined value 410, as previously described. As shown in FIG. 4, heart rate 414 begins to increase from initial value 420 as time progresses. At 424, heart rate 414 exceeds the first predetermined value 408. At 428, heart rate 414 exceeds the second predetermined value 410. In one embodiment, once heart rate 414 exceeds the second predetermined value 410, at 428, maximum ventricular pacing rate 442 is set to the first predetermined value 408. Heart rate 414 is then shown to decrease (i.e., drop). When heart rate 414 falls below a predetermined threshold, maximum ventricular pacing rate 442 is set to the second predetermined value 410. In one embodiment (as shown in FIG. 4), when heart rate 414 falls below the first predetermined value 408 at 440, maximum ventricular pacing rate 442 is set to the second predetermined value 410. In an alternative embodiment (not shown in FIG. 4), when heart rate 414 falls below the second predetermined value 410, maximum ventricular pacing rate 442 is set to the second predetermined value 410.

Figure 5:
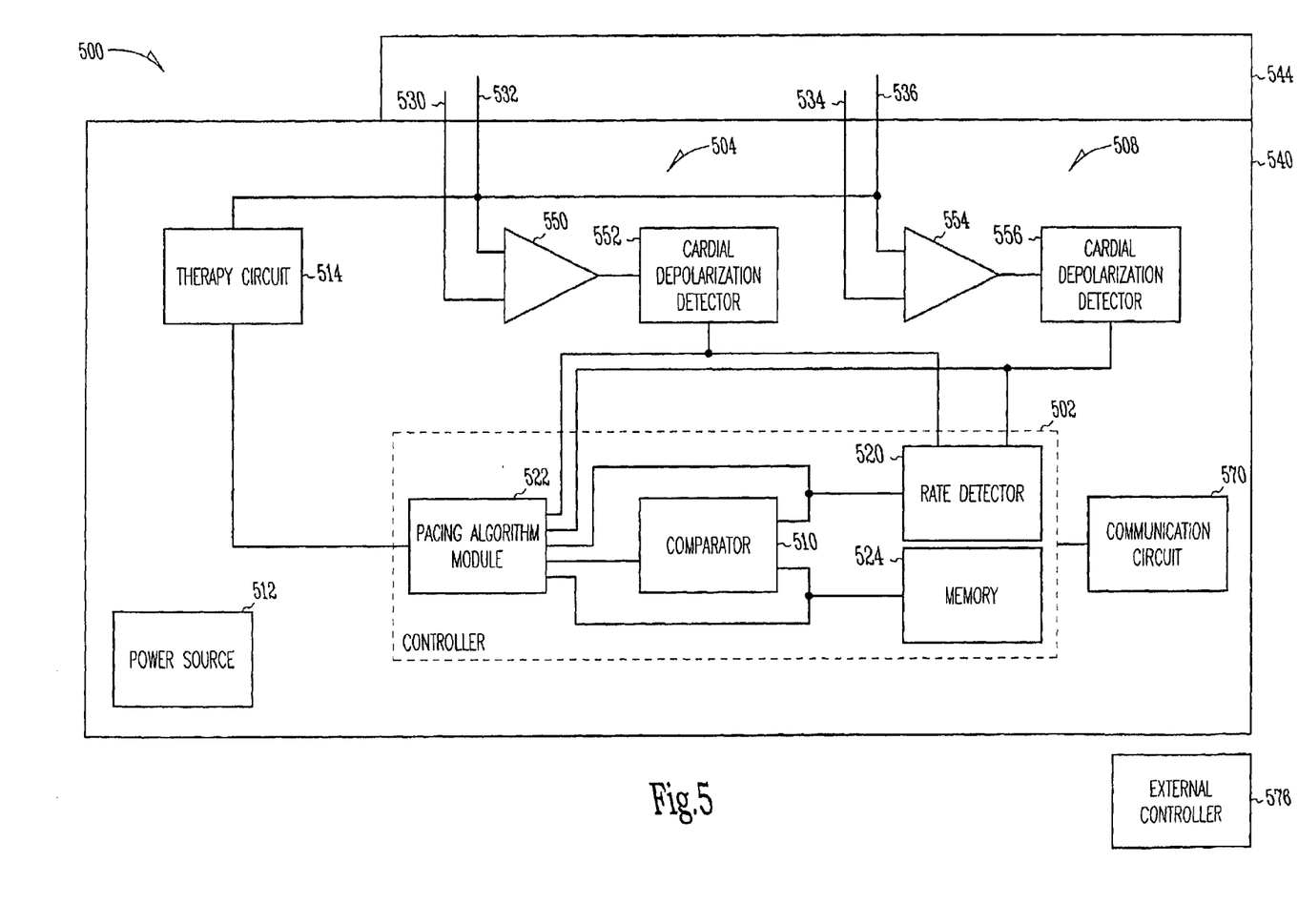
FIG. 5 is a block diagram of one embodiment of an cardiac rhythm management system according to the present subject matter.

Referring now to FIG. 5, there is shown a schematic diagram of a cardiac rhythm management system 500 according to one embodiment of the present subject matter. In one embodiment, system 500 includes circuitry which receives one or more cardiac signals and delivers electrical energy to electrodes positioned within a patient's heart. System 500 includes a first sensing circuit 504, a second sensing circuit 508, a controller 502, a therapy circuit 514, and a power source 512. In one embodiment, controller 502 is a microprocessor-based system, including a rate detector 520, a comparator 510, a pacing algorithm module 522, and a memory circuit 524. Memory circuit 524 contains parameters for various pacing and sensing modes and stores data indicative of cardiac signals received by the controller 502. In one embodiment, system 500 receives cardiac signals through connection terminals 530, 532, 534 and 536, which are coupled to the electrodes attached to intravascular endocardial leads (e.g., the first and second intravascular endocardial leads, as previously described).

A hermetically sealed housing 540 encases the implantable circuitry of system 500. Housing 540 is suitable for implantation in a human body. In one embodiment, the housing 540 is made of titanium. However, other biocompatible housing materials as are known in the art may also be used. A connector module 544, referred to as a header, is attached to housing 540 to allow for physical and electrical connections between the intravascular endocardial leads and the encased circuitry.

First sensing circuit 504 includes a first sense amplifier 550 and a first cardiac depolarization detector 552. Second sensing circuit 508 includes a second sense amplifier 554 and a second cardiac depolarization detector 556. First sensing circuit 504 is electrically coupled to terminals 530 and 532. Second sensing circuit 508 is electrically coupled to terminals 534 and 536. These terminals, in turn, are coupled to heart sites, via intravascular endocardial leads, to allow for the one or more cardiac signals to be sensed in the heart. In the present embodiment, first sensing circuit 504 receives a first cardiac signal, and second sensing circuit 508 receives a second cardiac signal. In one embodiment, one or more cardiac signals are sensed from an atrium and amplified. Atrial depolarizations, including P-waves, are detected and routed to controller 502. In one embodiment, one or more cardiac signals are sensed from one or more ventricles and amplified. Ventricular depolarizations, including R-waves, are detected and routed to controller 502. In one embodiment, one or more cardiac signals are sensed from an atrium and one or more ventricles and amplified. Atrial and ventricular depolarizations, including P-waves and R-waves, are detected and routed to controller 502.

Pacing algorithm module 522 responds to, among other things, sensing circuits 504 and 508 by providing pacing commands to therapy circuit 514, as needed according to the programmed pacing mode. In one embodiment, therapy circuit 514 delivers pacing pulses to one or more intravascular endocardial leads. Power to system 500 is supplied by power source 512. In one embodiment, power source 512 includes one or more electrochemical batteries.

In one embodiment, rate detector 520 determines a heart rate based on the cardiac depolarizations detected by depolarization detector 552 or depolarization detector 556. In one embodiment, rate detector 520 determines an atrial rate as the heart rate. In an alternative embodiment, rate detector 520 determines a ventricular rate as the heart rate.

Comparison circuit 510 receives the heart rate and compares the heart rate to the first predetermined value and the second predetermined value. The result of the comparison is routed to pacing algorithm module 522, which sets the maximum ventricular pacing rate to the first predetermined value when the heart rate exceeds the second predetermined value and sets the maximum ventricular pacing rate to the second predetermined value when the heart rate falls below a predetermined threshold, as previously described. In one embodiment, the predetermined threshold is set to the first predetermined value. In an alternative embodiment, the predetermined threshold is set to the second predetermined value. In a further embodiment, when pacing algorithm module 522 changes the maximum ventricular pacing rate from the second predetermined value to the first predetermined value, it does so over a predetermined time interval when the heart rate exceeds the second predetermined value.

In an additional embodiment, pacing algorithm module 522 sets the PVARP based on the first predetermined value and the second predetermined value. In one embodiment, pacing algorithm module 522 sets the PVARP to a first set value when the maximum ventricular pacing rate is set to the first predetermined value, and sets the PVARP to a second set value when the maximum ventricular pacing rate is set to the second predetermined value. In one embodiment, the PVARP is set to a first set value at the LRL, and is set to a second set value at the hysteresis MTR, and is set to a value between the first and second set values in correspondence with the distances of the determined heart rate from the LRL and the hysteresis MTR, as previously described. In an alternative embodiment, the PVARP associated with each MTR can be set such that the sum of the PVARP and the AV delay is equal to the predetermined MTR interval minus a programmable sensing window interval, as previously described. In another alternative embodiment, controller 502 sets the maximum ventricular pacing rate to the first predetermined value when an atrial depolarization is detected during the PVARP. In still another alternative embodiment, controller 502 sets the maximum ventricular pacing rate to the first predetermined value when atrial depolarizations are detected during the respective PVARPs over a predetermined number of consecutive cardiac cycles. In yet another alternative embodiment, controller 502 sets the maximum ventricular pacing rate to the first predetermined value when atrial depolarizations are detected during the respective PVARPs in at least a predetermined number of cardiac cycles over a predetermined total number of consecutive cardiac cycles.

In an additional embodiment, pacing algorithm module 522 extends the PVARP having the first set value for at least one cardiac cycle length after setting the maximum ventricular pacing rate to the first predetermined value when the heart rate exceeds the second predetermined value to protect against sensing retrograde atrial events. In a further embodiment, controller 502 ignores the atrial depolarizations and does not trigger the AV delay for one cardiac cycle every N cardiac cycles when the heart rate is above the first predetermined value. This assists in stopping PMT, as previously described. In an additional embodiment, when therapy circuit 514 delivers ventricular pacing pulses at the second maximum pacing rate, pacing algorithm module 522 sets the maximum ventricular pacing rate to the first predetermined value.

In one embodiment, a communication circuitry 570 is additionally coupled to controller 502 to allow system 500 to communicate with an external programmer 576. In one embodiment, communication circuitry 570 includes a data receiver and a data transmitter to receive and transmit signals, including cardiac data, to and from external programmer 576. In one embodiment, the data receiver and the data transmitter include a wire loop antenna to establish a radio frequency telemetry link, as is known in the art, to receive and transmit signals and data to and from external programmer 576.

It is understood that the above description is intended to be illustrative, and not restrictive. Many other embodiments will be apparent to those of skill in the art upon reviewing the above description. The scope of the invention should therefore, be determined with reference to the appended claims, along with the full scope of equivalents to which such claims are entitled.

What is claimed is:

1. A method, including:
   sensing a first cardiac signal from a ventricular location;
   detecting ventricular depolarizations from the first cardiac signal;
   determining a heart rate based on the ventricular depolarizations;
   comparing the heart rate to a first predetermined value and a second predetermined value, the second value larger than the first value;
   setting a maximum ventricular pacing rate to the first predetermined value when the heart rate exceeds the second predetermined value; and
   setting the maximum ventricular pacing rate to the second predetermined value when the heart rate falls below a predetermined threshold.

2. The method of claim 1, wherein the maximum ventricular pacing rate is a maximum tracking rate (MTR).

3. The method of claim 1, wherein the predetermined threshold is set to the first predetermined value.

4. The method of claim 1, wherein the predetermined threshold is set to the second predetermined value.

5. The method of claim 1, wherein setting the maximum ventricular pacing rate to the first predetermined value when the heart rate exceeds the second predetermined value includes changing the maximum ventricular pacing rate from the second predetermined value to the first predetermined value over a predetermined time interval.

6. The method of claim 1, further including:
   sensing a second cardiac signal from an atrial location;
   detecting atrial depolarizations from the second cardiac signal;
   setting the PVARP to a first set value when the maximum ventricular pacing rate is set to the first predetermined value; and
   setting the PVARP to a second set value when the maximum ventricular pacing rate is set to the second predetermined value.

7. The method of claim 6, further including:
   calculating the first predetermined value based on at least the first set value and an atrioventricular pacing delay (AV delay); and
   calculating the second predetermined value based on at least the second set value and the AV delay.

8. The method of claim 6, further including:
   calculating the first predetermined value based on at least the first set value, an AV delay, and a first sensing window interval; and
   calculating the second predetermined value based on at least the second set value, the AV delay, and a second sensing window interval.

9. The method of claim 8, wherein:
   the first sensing window interval is a predetermined percentage of a sum of the first set value and the AV delay; and
   the second sensing window interval is a predetermined percentage of a sum of the second set value and the AV delay.

10. The method of claim 8, wherein the sensing window interval is a programmable value being a function of at least one of the first and second predetermined values.

11. The method of claim 6, further including extending the PVARP associated with the first predetermined value for at least one cardiac cycle length after setting the maximum ventricular pacing rate to the first predetermined value when the heart rate exceeds the second predetermined value.

12. The method of claim 6, further including calculating the second predetermined value from the PVARP and an AV delay.

13. The method of claim 1, further including:
   sensing a second cardiac signal from an atrial location;
   detecting atrial depolarizations from the second cardiac signal; and
   ignoring any atrial depolarization and not triggering an AV delay for one cardiac cycle every N cardiac cycles when the heart rate exceeds the first predetermined value.

14. The method of claim 1, further including:
   sensing a second cardiac signal from an atrial location;
   detecting atrial depolarizations from the second cardiac signal; and
   setting the maximum ventricular pacing rate to the first predetermined value when an atrial depolarization is sensed during a postventricular atrial refractory period (PVARP).

15. The method of claim 1, further including:
   sensing a second cardiac signal from an atrial location;
   detecting atrial depolarizations from the second cardiac signal; and
   setting the maximum ventricular pacing rate to the first predetermined value when at least a predetermined number of atrial depolarizations are sensed during postventricular atrial refractory periods (PVARPS) over a predetermined number of consecutive cardiac cycles.

16. The method of claim 1, further including:
   delivering ventricular pacing pulses; and
   setting the maximum ventricular pacing rate to the first predetermined value when the ventricular pacing pulses are delivered at a rate equal to the second predetermined value.

17. A cardiac rhythm management system, including:
a first lead adapted to sense a first cardiac signal in or about a ventricle of a heart;
a first sensing circuit, coupled to the first lead, including:
- a first sense amplifier, coupled to the first lead, to receive the first cardiac signal; and
- a first cardiac depolarization detector, coupled to the first sense amplifier, to detect ventricular depolarizations in the first cardiac signal;

a controller, coupled to the first sensing circuit, including:
- a rate detector, coupled to the first cardiac depolarization detector, to
- determine a heart rate from detected ventricular depolarizations,
- a comparator, coupled to the rate detector, including inputs representative of the heart rate and at least one of a first predetermined value, a second predetermined value, and a predetermined threshold and one or more outputs representative of whether the heart rate exceeds the second predetermined value and whether heart rate falls below the predetermined threshold;
- a storage medium, coupled to the comparator, including the first predetermined value, the second predetermined value, and the predetermined threshold; and
- a pacing algorithm module, coupled to the comparator, to set a maximum ventricular pacing rate to the first predetermined value when the heart rate exceeds the second predetermined value, and set the maximum ventricular pacing rate to the second predetermined value when the heart rate falls below a predetermined threshold.

18. The cardiac rhythm management system of claim 17, wherein the maximum ventricular pacing rate is a maximum tracking rate (MTR).

19. The cardiac rhythm management system of claim 17, wherein the predetermined threshold is equal to the first predetermined value.

20. The cardiac rhythm management system of claim 17, wherein the predetermined threshold is equal to the second predetermined value.

21. The cardiac rhythm management system of claim 17, further including:
a second lead adapted to sense a second cardiac signal in or about an atrium of a heart; and
a second sensing circuit, coupled to the second lead, including:
- a second sense amplifier, coupled to the second lead, to receive the second cardiac signal; and
- a second cardiac depolarization detector, coupled to the second sense amplifier, to detect atrial depolarizations in the second cardiac signal.

22. The cardiac rhythm management system of claim 21, further including a therapy circuit, coupled to the controller, to deliver pacing pulses to the heart via at least one of the first and second leads.

* * * * *

UNITED STATES PATENT AND TRADEMARK OFFICE
CERTIFICATE OF CORRECTION

| | | |
|---|---|---|
| PATENT NO. | : 6,904,316 B2 | Page 1 of 1 |
| APPLICATION NO. | : 10/012887 | |
| DATED | : June 7, 2005 | |
| INVENTOR(S) | : Andrew P. Kramer | |

It is certified that error appears in the above-identified patent and that said Letters Patent is hereby corrected as shown below:

In column 14, line 59, In Claim 15, delete "(PVARPS)" and insert - - (PVARPs) - -, therefor.

Signed and Sealed this

Twenty-second Day of August, 2006

JON W. DUDAS
*Director of the United States Patent and Trademark Office*